United States Patent [19]
Lobdell

[11] Patent Number: 4,978,446
[45] Date of Patent: Dec. 18, 1990

[54] STERILE BLOOD COMPONENT COLLECTION

[75] Inventor: Donn D. Lobdell, Englewood, Colo.

[73] Assignee: Cobe Laboratories, Inc., Lakewood, Colo.

[21] Appl. No.: 467,034

[22] Filed: Jan. 18, 1990

Related U.S. Application Data

[63] Continuation of Ser. No. 322,097, Mar. 10, 1989, abandoned, which is a continuation of Ser. No. 89,493, Aug. 26, 1987, abandoned.

[51] Int. Cl.[5] ...................... B01D 35/02; B01D 36/00; B01D 63/08; B01D 65/00
[52] U.S. Cl. .................................... 210/206; 210/295; 210/321.6; 210/446; 494/36; 604/406; 604/408
[58] Field of Search .................. 604/4, 5, 6, 406, 408; 494/36; 210/198.1, 205, 257.2, 295, 321.6, 321.84, 435, 446, 206, 360.1

[56] References Cited

U.S. PATENT DOCUMENTS

| | | | |
|---|---|---|---|
| 3,932,153 | 1/1976 | Byrns | 210/446 |
| 4,197,847 | 4/1980 | Djerassi | 604/6 |
| 4,223,672 | 9/1980 | Terman et al. | 604/5 |
| 4,259,187 | 3/1981 | DeFrank et al. | 210/446 |
| 4,265,760 | 5/1981 | Abel et al. | 210/321.84 |
| 4,294,594 | 10/1981 | Sloane, Jr. et al. | 210/446 |
| 4,326,957 | 4/1982 | Rosenberg | 210/446 |
| 4,346,703 | 8/1982 | Dennehey et al. | 604/406 |
| 4,444,661 | 4/1984 | Jackson et al. | 210/446 |
| 4,695,382 | 9/1987 | Cronin | 604/406 |

OTHER PUBLICATIONS

"Closed System Apheresis Kit for Extended Platelet Storage", Fenwal Laboratories, 1984.
McDonald, H. Jr., "An Automatic Peritoneal Dialysis Machine for Hospital or Home Peritoneal Dialysis: A Preliminary Report", vol. XV, Trans. Amer. Soc. Artif. Int. Organs (1969), pp. 108–111.

*Primary Examiner*—W. Gary Jones

[57] ABSTRACT

Apparatus for collecting blood components including a supply line that is connected to a blood line and has a filter on it to permit passage of supply solution (e.g., anticoagulant or saline prime) and blocks passage of bacteria.

8 Claims, 1 Drawing Sheet

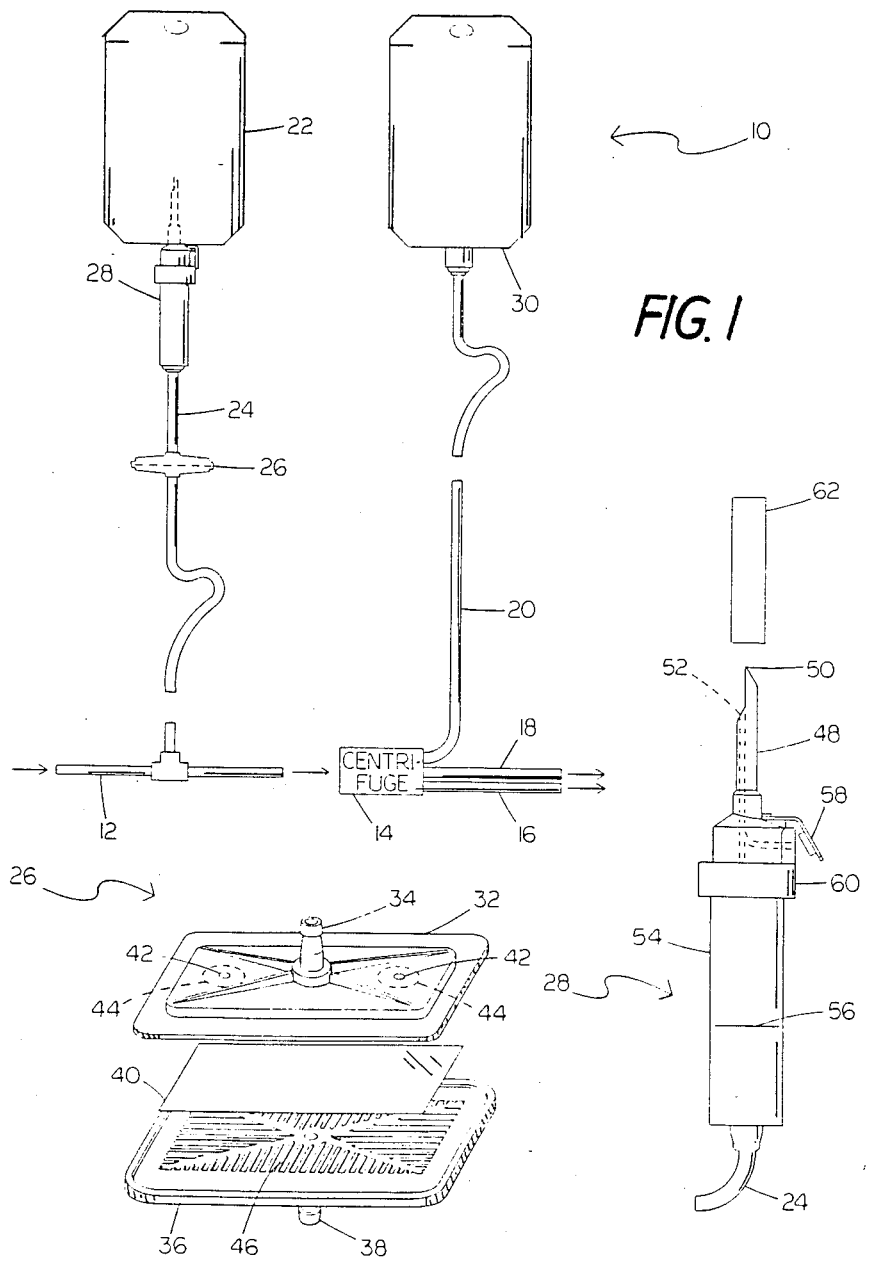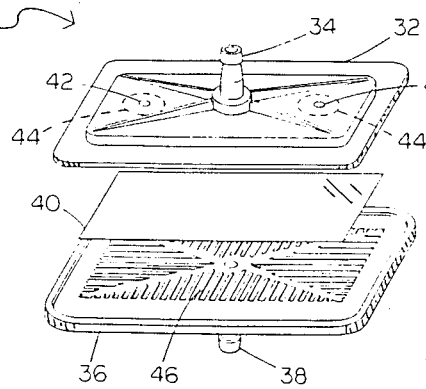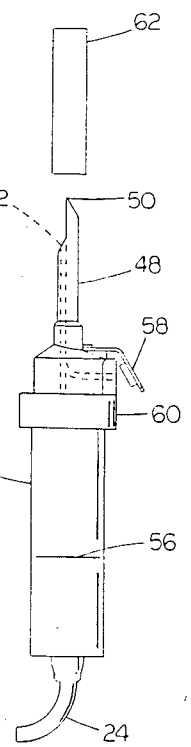
FIG. 1
FIG. 2
FIG. 3

STERILE BLOOD COMPONENT COLLECTION

This application is a division of application Ser. No. 322,097 filed Mar. 10, 1989, now abandoned which is a continuation of application Ser. No. 089,493 filed Aug. 26, 1987, of Donn D. Lobdell for STERILE BLOOD COMPONENT COLLECTION, now abandoned.

FIELD OF THE INVENTION

The invention relates to apparatus for collecting components from a donor's blood.

BACKGROUND OF THE INVENTION

In blood component separation and collection apparatus, for example, a centrifuge, it is desired to prevent the introduction of bacteria into the collection bags for the blood components separated from a donor's blood. In at least some prior blood centrifuge systems, a disposable tubing set for use with each donor includes anticoagulant and saline priming solutions in bags preconnected to the blood supply line.

SUMMARY OF THE INVENTION

It has been discovered that a supply solution (e.g., anticoagulant or saline prime) could be supplied to a blood flow line from a donor in a manner to maintain a sterile system by providing a filter in the supply line to permit passage of the supply solution and block passage of bacteria.

In preferred embodiments the supply line has a connector upstream of the filter for connection to a source of supply solution; the connector has a needle for piercing a bag of supply solution; the filter includes a membrane with a maximum pore size to prevent passage of bacteria; and the blood flow line is connected to a separation channel of a centrifuge having an outlet line connected to a platelet collection bag.

Other advantages and features of the invention will be apparent from the following description of a preferred embodiment thereof and from the claims.

DESCRIPTION OF THE PREFERRED EMBODIMENT

The preferred embodiment will now be described.

Drawings

FIG. 1 is a diagram of platelet collection apparatus according to the invention.

FIG. 2 is an exploded perspective view of a filter of the FIG. 1 apparatus.

FIG. 3 is an exploded elevation of a connector of the FIG. 1 apparatus.

Structure

Referring to FIG. 1, there is shown platelet collection apparatus 10, including blood supply line 12, centrifuge 14 and outlet tubes 16, 18, 20. Anticoagulant supply bag 22 is connected to blood supply line 12 via supply line 24, having filter 26 on it and connected to anticoagulant bag 22 by connector 28. Outlet tube 20 is connected to platelet collection bag 30. Centrifuge 14 includes a rotating bowl that receives a disposable channel connected to tubes 12, 16, 18, 20 and is similar to the centrifuge apparatus described in Kellogg et al. U.S. Pat. No. 4,387,848, which is hereby incorporated by reference. Tubes 12, 16, 18, 20 are connected to the channel by a seal-less multichannel rotation connection means of the type shown in U.S. Pat. No. 4,146,172 (incorporated by reference), maintaining the closed, bacteria-free system.

Referring to FIG. 2, it is seen that filter 26 includes upper housing 32 with inlet 34, lower housing 36 with outlet 38 and microporous membrane 40 therebetween. Filter 26 is available from Gelman Filters. Membrane 40 (available under the trade designation VERSAPOR 200) has a 0.2 micron pore size. Upper housing 32 also has vent holes 42 covered by membranes 44 carried on the lower surface of housing 32. Lower housing 36 has ribs 46 to support membrane 40 and to provide drainage channels between them directed into the opening to outlet 38.

Referring to FIG. 3, connector 28 includes needle 48, having sharp pointed end 50 for piercing a wall of bag 22 and fluid flow passage 52 therein. Needle 48 is connected to clear plastic drip chamber 54 having fluid level indicia 56. Cap 58 is removably connectable to cover a vent hole in base 60, formed integrally with needle 48. Cover 62 covers needle 48.

Apparatus 10 also includes a supply bag of saline prime solution connected to blood flow line 12 by a filter and supply tube (all not shown) similar to that for anticoagulant.

Operation

In operation, when centrifuge 14 is used with a new donor, a sterile tubing set including tubes 12, 16, 18, 20, 24 and a centrifuge channel (not shown) is mounted on centrifuge 14, and connector 28 is connected to anticoagulant bag 22 by puncturing bag 22 with needle 48 after removing needle cover 62. A sterile saline prime solution bag (not shown) is connected in a similar manner. During the removal of cover 62 and the connection of connector 28 to bag 22, it is possible that the hydraulic system is exposed to bacteria at connector 28. Any bacteria introduced into connector 28 are prevented from going past filter 26, owing to the pore size of membrane 40. Bacteria are thus prevented from being transported to platelet collection bag 30, where they could otherwise multiply during storage of the platelets. By providing filters and connectors on the tubing set, the supplies of anticoagulant and sterile solution can be shipped and stored separately from the tubing set, simplify, shipping, storage, and handling of the tubing set. In addition, different fluids and different bag volumes can be selected, depending upon a particular donor's need, and the solutions and tubing set can each be separately sterilized by a method most appropriate for each.

Puncturing needle 48 can be used multiple times during a given procedure to connect multiple bags. Thus the amounts of both saline and anticoagulant that are actually needed can be provided. This is an advantage over permanently connected bags, which either limit the procedure to the amount of solution preconnected or tend to oversize the amount of fluid furnished with the set, which leads to both higher weights and wastage of fluid. This feature also permits flexibility to extend a procedure that is not proceeding as quickly as expected in terms of collection. The procedure can be extended until the desired amount of blood components have been collected, adding a new bag of anticoagulant as needed.

OTHER EMBODIMENTS

Other embodiments of the invention are within the scope of the following claims.

For example, other blood separators besides centrifuge 14 can be used, and the invention is applicable to collecting other blood components.

What is claimed is:

1. Apparatus for collecting blood components comprising
    a sterile fluid flow line for receiving blood from a donor,
    a blood separator including a disposable separation channel connected to said flow line to receive and separate said blood,
    a blood component collection container connected to said separator via an outlet line,
    a first supply line connected at one end to supply solution to said sterile fluid flow line, the other end of said supply line being connected to a connector adapted to be connected to a source of said solution, and
    a first filter on said supply line that includes means for permitting passage of said solution and blocking passage of bacteria,
    said sterile fluid flow line, first supply line, separation channel, outlet line, and blood component collection chamber being permanently connected together to maintain a closed, bacteria-free system downstream of said filter,
    whereby said source of solution can be connected to said connector at the time of use without bacteria being transmitted into said sterile flow line, separator and collection container.

2. The apparatus of claim 1 wherein said connector includes a needle for puncturing a wall of a source of supply solution.

3. The apparatus of claim 2 wherein said connector has a drip chamber attached to it.

4. The apparatus of claim 1 wherein said filter comprises a membrane having a maximum pore size to prevent passage of bacteria.

5. The apparatus of claim 1 wherein said supply solution is anticoagulant or saline prime solution.

6. The apparatus of claim 1 wherein said blood separator is a centrifuge.

7. The apparatus of claim 1 wherein said blood component collection container is a platelet collection bag.

8. The apparatus of claim 1 further comprising a second supply line connected at one end to supply solution to said sterile fluid flow line and a second filter on said supply line that includes means for permitting passage of solution and blocking passage of bacteria.

* * * * *